(12) United States Patent
Vizitiu et al.

(10) Patent No.: US 7,501,514 B1
(45) Date of Patent: Mar. 10, 2009

(54) ENANTIOMERIC RESOLUTION OF 2-SUBSTITUTED 4-SUBSTITUTED 1,3-OXATHIOLANES NUCLEOSIDES

(75) Inventors: Dragos Vizitiu, Edmonton (CA); Dan Simion, Edmonton (CA); Ioana R. Simion, legal representative, Edmonton (CA); Jean-Eric Lacoste, Laval (CA)

(73) Assignee: Shire Biochem, Inc., Quebec (CA)

( * ) Notice: Subject to any disclaimer, the term of this patent is extended or adjusted under 35 U.S.C. 154(b) by 509 days.

(21) Appl. No.: 10/964,975

(22) Filed: Oct. 15, 2004

Related U.S. Application Data

(60) Provisional application No. 60/511,099, filed on Oct. 15, 2003.

(51) Int. Cl.
*C07D 409/04* (2006.01)
(52) U.S. Cl. ................................. 544/317
(58) Field of Classification Search ............ 544/317
See application file for complete search history.

(56) References Cited

U.S. PATENT DOCUMENTS

| | | | |
|---|---|---|---|
| 4,994,604 A | 2/1991 | Tung et al. | |
| 5,302,751 A | 4/1994 | Manimaran et al. | |
| 6,022,409 A | 2/2000 | Coquerel et al. | |
| 6,228,860 B1 * | 5/2001 | Mansour et al. | 514/263.23 |
| 6,600,044 B2 * | 7/2003 | Murthy et al. | 544/264 |

FOREIGN PATENT DOCUMENTS

| WO | WO 92/08717 | 5/1992 |
|---|---|---|
| WO | WO 95/29176 | 11/1995 |
| WO | WO 02/102796 | 12/2002 |

* cited by examiner

*Primary Examiner*—Deepak Rao
(74) *Attorney, Agent, or Firm*—Millen, White, Zelano & Branigan, P.C.

(57) ABSTRACT

Single enantionmers of compounds of formula (B), in either the cis or trans configuration,

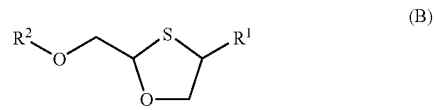

(B)

wherein $R^1$ and $R^2$ are as defined herein, can be separated from enantiomeric mixtures thereof by reacting the compound with an acid to produce a conglomerate salt that has the following characteristics:
the IR spectrum of the salt of the racemic compound, a 1:1 mixture of (−) and (+) crystals, is identical to that of the each of the single enantiomer, and
the salt of the racemic compound has a melting point lower that that of either single enantiomer. The conglomerate salt is then separated by preferential crystallization.

23 Claims, 2 Drawing Sheets

Phase diagram for the conglomerate with p-Toluenesulfonic acid

ENANTIOMERIC RESOLUTION OF 2-SUBSTITUTED 4-SUBSTITUTED 1,3-OXATHIOLANES NUCLEOSIDES

This application claims the benefit of U.S. Provisional Application Ser. No. 60/511,099, filed Oct. 15, 2003, which is hereby incorporated in its entirety.

FIELD OF THE INVENTION

The present invention relates to a novel process for producing (−) and (+) isomers of cis nucleosides or nucleoside analogues and derivatives of formula (A):

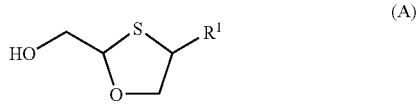

wherein $R^1$ is a pyrimidine base or a pharmaceutically acceptable derivative.

BACKGROUND OF THE INVENTION

Classes of compounds of formula (A), particularly the 2-substituted 4-substituted 1,3-oxathiolanes pyrimidine nucleosides have been found to have potent antiviral activity. In particular, these compounds have been found to act as potent inhibitors of HIV-1 replication in T-lymphocytes over a prolonged period of time with less cytotoxic side effects than compounds known in the art (see Belleau et al (1993) Bioorg. Med. Chem. Lett. Vol. 3, No. 8, pp. 1723-1728). These compounds have also been found active against 3TC-resistant HIV strains (see Taylor et al (2000) Antiviral Chem. Chemother. Vol 11, No. 4, pp. 291-301; Stoddart et al (2000) Antimicrob. Agents Chemother. Vol. 44, No. 3, pp. 783-786). These compounds are also useful in prophylaxis and treatment of hepatitis B virus infections.

Methods for the preparation of these compounds have been disclosed in PCT publications WO 92/08717, WO 95/29176 and WO 02/102796 as well as in publications by Belleau et al (1993) Bioorg. Med. Chem. Lett. Vol. 3, No. 8, pp. 1723-1728; Wang et al (1994) Tetrahedron Lett. Vol. 35, No. 27, pp. 4739-4742; Mansour et al, (1995) J. of Med. Chem. Vol. 38, No. 1, pp. 1-4 and Caputo et al in Eur. J. Org. Chem. Vol. 6, pp. 1455-1458 (1999).

The product of the existing processes is in many cases a racemate. This racemate normally requires further processing to obtain the pure enantiomers. A preferred method for the production of single enantiomers is resolution of the racemate such as by direct preferential crystallization, crystallization of the diastereomeric salts, kinetic resolution, enzymatic resolution, selective absorption and asymmetric synthesis.

If the racemate is a true racemic compound, a homogeneous solid phase of the two enantiomers co-exists in the same cell unit. These materials may be separated via diastereomer crystallization, which generally involves reacting the racemate with an optically pure acid or base (the resolving agent) to form a mixture of diastereomeric salts that are then separated by crystallization. Other racemates may exist in the form of conglomerates, which is a compound that crystallizes with a single enantiomer in the crystal lattice. However, conglomerates are observed in less than 20% of all racemates. A conglomerate can be defined as an equimolar mixture of two crystalline enantiomers that are, in principle, mechanically separable. The phase diagram of a conglomerate displays one sharply defined minimum temperature at a mixture of 50% and 50% that is the eutectic point of the enantiomeric mixture. The success of a preferential crystallization depends on this fact.

Methods for resolving certain racemates by formation of conglomerate salts, also known as preferential crystallization or resolution by entrainment, are described in, for example, Tung et al. (U.S. Pat. No. 4,994,604), Manimaran et al. (U.S. Pat. No. 5,302,751), and Coquerel et al. (U.S. Pat. No. 6,022,409), the entire disclosures of which are hereby incorporated by reference.

A conglomerate compound crystallizes as a single enantiomer in the crystal lattice. Therefore, to be a conglomerate the IR spectrum of the racemic conglomerate salt, a 1:1 mixture of (−) and (+) crystals, must be identical to that of the single enantiomer. Another characteristic of conglomerate behavior is that the racemic conglomerate salt normally has a melting point lower that that of either single enantiomer.

If a conglomerate is obtained, it may be used for enantiomeric excess enhancement because the most soluble composition is racemic. Generally the conglomerate of X % enantiomeric excess will provide an X % yield of single enantiomer leaving behind racemic liquors.

A conglomerate may also be used in an entrainment process in which a racemic solution is seeded with a single enantiomer leading to preferential kinetic precipitation of that enantiomer.

SUMMARY OF THE INVENTION

The process object of the present invention is the preparation of single enantiomers of compounds of formula (B) in the cis configuration

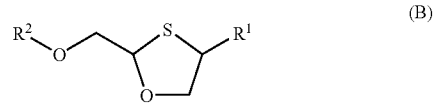

wherein
$R^1$ is pyrimidine base or a pharmaceutically acceptable derivative thereof,
$R^2$ is hydrogen or a carboxyl function $R^3$—(CO); and
$R^3$ is selected from hydrogen, straight or branched chain (e.g., methyl, ethyl, n-propyl, t-butyl, n-butyl) or cyclic alkyl, alkoxyalkyl (e.g., methoxymethyl), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy), substituted dihydro pyridinyl (e.g., N-methyldihydro pyridinyl), sulphonate esters such as alkyl- or aralkylsulphonyl (e.g., methanesulphonyl), sulfate esters, amino acid esters (e.g., L-valyl or L-isoleucyl) and mono, di- or triphosphate esters, and pharmaceutically acceptable salts and esters thereof:

comprising forming a conglomerate salt of racemic mixture or an enantiomerically enriched mixture of Compound (B) with an acid wherein the resulting conglomerate salt that has the following characteristics:

the IR spectrum of the salt of the racemic compound, a 1:1 mixture of (−) and (+) crystals, is identical to that of each of the single enantiomer, and the salt of the racemic compound has a melting point lower that that of either single enantiomer; an enantiomerically enriched mixture of the salts of the enantiomers is obtained by crystallization, the free base of the enantiomerically enriched mixture is then obtained by standard methods.

Following formation of the conglomerate salt, the enantiomers can be separated by preferential crystallization such as described in Tung et al. (U.S. Pat. No. 4,994,604), Manimaran et al. (U.S. Pat. No. 5,302,751), and Coquerel et al. (U.S. Pat. No. 6,022,409).

This process may also be used to prepare the single enantiomers of Compound (B) in the trans configuration.

In an alternative embodiment of the present invention, the conglomerate salt of cis 2'-deoxy-3'-oxa-4'-thiocytidine is formed, wherein the single enantiomer shows a much lower solubility than the racemate in polar solvents is disclosed.

The present invention includes the direct enantiomer separation of enantiomeric mixtures of cis 2'-deoxy-3'-oxa-4'-thiocytidine or cis/trans combinations of 2'-deoxy-3'-oxa-4'-thiocytidine without the need for resolving agents, by seeding a supersaturated solution of the 2'-deoxy-3'-oxa-4'-thiocytidine conglomerate salt with the desired single enantiomer 2'-deoxy-3'-oxa-4'-thiocytidine conglomerate salt, under controlled conditions.

DETAILED DESCRIPTION OF THE INVENTION

Accordingly, there is a provided in a first aspect of this invention the preparation of a single enantiomer of compounds of formula (B) in the cis configuration

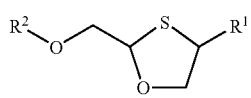

(B)

wherein $R^1$ and $R^2$ are as defined above, and pharmaceutically acceptable salts and esters thereof, via the formation of a conglomerate salt of a racemic mixture or an enantiomerically enriched mixture of Compound (B) with an acid wherein the resulting conglomerate salt has the following characteristics: an IR spectrum of a the salt of the racemic compound, a 1:1 mixture of (−) and (+) crystals, which is identical to each of the single enantiomer, and the salt of the racemic compound has a melting point lower that that of either single enantiomer.

The present invention is based on the formation of a conglomerate salt of 2-substituted 4-substituted 1,3-oxathiolanes of formula (B) wherein $R^1$ is pyrimidine base or a pharmaceutically acceptable derivative thereof and $R^2$ is hydrogen or a carboxyl function $R^3$—(CO) in which the non-carbonyl moiety $R^3$ of the ester grouping is selected from hydrogen, straight or branched chain alkyl (e.g., methyl, ethyl, n-propyl, t-butyl, n-butyl), $C_{3-8}$ cyclic alkyl, alkoxyalkyl (e.g., methoxymethyl), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy); substituted dihydro pyridinyl (e.g., N-methyldihydro pyridinyl), sulphonate esters such as alkyl- or aralkylsulphonyl (e.g., methanesulphonyl), sulfate esters, amino acid esters (e.g., L-valyl or L-isoleucyl) and mono, di- or triphosphate esters.

Preferably, $R^1$ is selected from the following formulae:

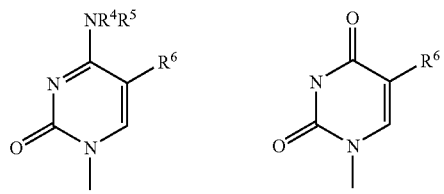

wherein
  $R^4$ and $R^5$ are in each case independently H, straight, branched or cyclic $C_{1-6}$ alkyl, straight, branched or cyclic $C_{2-6}$ alkenyl, $C_{6-14}$ aryl, or $C_{5-10}$ heteroaromatic ring containing 1-3 heteroatoms selected from the group comprising O, N, or S; and
  $R^6$ is selected from the group consisting of hydrogen, hydroxymethyl, trifluoromethyl, straight, branched or cyclic $C_{1-6}$ alkyl, straight, branched or cyclic $C_{2-6}$ alkenyl, bromine, chlorine, fluorine, and iodine.

$R^1$ may be, for example, cytosine or 5-fluorocytosine.

$R^2$ also includes esters derived from polyfunctional acids such as carboxylic acids containing more than one carboxyl group, for example, dicarboxylic acids $HO_2C(CH_2)_n CO_2H$ where n is an integer of 1 to 10 (for example, succinic acid) or phosphoric acids. Methods for preparing such esters are well known. See, for example, E. Hahn et al., "Nucleotide dimers as anti-human immunodeficiency virus agents", Nucleotide Analogues As Antiviral Agents, J. C. Martin, Ed. Symposium Series #401, American Chemical Society, pp. 156-159 (1989) and M. Busso et al., "Nucleotide dimers suppress HIV expression in vitro", AIDS Research and Human Retroviruses, 4(6), pp. 449-455 (1988).

The present invention includes the formation of a conglomerate salt of cis 2'-deoxy-3'-oxa-4'-thiocytidine wherein the single enantiomer shows a much lower solubility than the racemate in polar solvents. Direct enantiomer separation, without the need for resolving agents, can be achieved by seeding a supersaturated solution of the racemate with a single enantiomer, under controlled conditions. The separation may also be achieved for any derivative thereof.

An embodiment of the present invention includes a method for resolving cis-2-hydroxymethyl-4-(cytosin-1'-yl)-1,3-oxathiolane or derivatives or salts thereof comprising:

a) reacting said cis-2-hydroxymethyl-4-(cytosin-1'-yl)-1,3-oxathiolane with an achiral acid to produce cis-2-hydroxymethyl-4-(cytosin-1'-yl)-1,3-oxathiolane.achiral acid salt;

b) preparing a solution of cis-2-hydroxymethyl-4-(cytosin-1'-yl)-1,3-oxathiolane.achiral acid salt having an enantiomeric excess greater than zero;

c) adding to said solution an amount of (+) or (−)-cis-2-hydroxymethyl-4-(cytosin-1'-yl)-1,3-oxathiolane.achiral acid salt sufficient to initiate crystallization;

d) recovering substantially one of said (+) or (−)-cis-2-hydroxymethyl-4-(cytosin-1'-yl)-1,3-oxathiolane.achiral acid salt;

e) converting said (+) or (−)-cis-2-hydroxymethyl-4-(cytosin-1'-yl)-1,3-oxathiolane.achiral acid salt into said (+) or (−)-cis-2-hydroxymethyl-4-(cytosin-1'-yl)-1,3-oxathiolane or salts.

Examples of achiral acids useful in the formation of conglomerate salts include hydrochloric acid (HCl), hydrobromic acid (HBr), sulfuric acid ($H_2SO_4$), tetrafluoroboric acid ($HBF_4$), methanesulfonic acid ($CH_3SO_3H$), benzenesulfonic (BS) acid ($C_6H_5SO_3H$), p-toluenesulfonic acid (p-$CH_3C_6H_4SO_3H$), p-aminoBS acid (p-$NH_2C_6H_4SO_3H$), p-chloroBS acid (p-$ClC_6H_4SO_3H$), p-hydroxyBS acid (p-$HOC_6H_4SO_3H$), chloroacetic acid ($ClCH_2COOH$), dichloroacetic acid ($Cl_2CHCOOH$), trichloroacetic acid ($Cl_3CHCOOH$), glycolic acid ($HOCH_2COOH$), pyruvic acid ($CH_3COCOOH$), succinic acid ($HOOC(CH_2)_2COOH$), adipic acid, ($HOOC(CH_2)_4COOH$), maleic acid (Cis-HOOCCH=CHCOOH), fumaric acid (Tr-HOOCCH=CHCOOH), citric acid ($HOC(CO_2H)(CH_2CO_2H)_2$) among others.

By the term "derivative" is a compound which may give rise to a pharmaceutically acceptable salt, ester, or salt of such ester of a compound of formula (B), or any other compound which, upon administration to the recipient, is capable of providing (directly or indirectly) a compound of formula (B) or an antivirally active metabolite or residue thereof. It will be appreciated by those skilled in the art that the compounds of formula (B) may be modified to provide pharmaceutically acceptable derivatives thereof, at functional groups in the base moiety.

The term "alkyl", as used herein, unless otherwise specified, refers to a saturated straight, branched, or cyclic, primary, secondary, or tertiary hydrocarbon of $C_{1-30}$, particularly $C_{1-6}$, unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro. It specifically includes methyl, ethyl, cyclopropyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "acyl", as used hereinafter refers to a functional group derived from an aliphatic carboxylic acid, by removal of the —OH group of 1 to 30 carbon atoms, particularly 1 to 6 carbon atoms. Like the acid to which it is related, an aliphatic acyl radical may be substituted (by a hydroxy, $N_3$, CN, halogen (F, Cl, Br, I), $C_{6-12}$ aryl, $C_{1-6}$ alkyl, $C_{2-12}$ alkoxyalkyl or nitro) or unsubstituted, and whatever the structure of the rest of the molecule may be, the properties of the functional group remain essentially the same (e.g., acetyl, propionyl, isobutanoyl, pivaloyl, hexanoyl, butyryl, pentanoyl, 3-methylbutyryl, hydrogen succinate, mesylate, valeryl, caproic, caprylic, capric, lauric, myristic, palmitic, stearic, oleic, 3-chlorobenzoate, trifluoroacetyl, chloroacetyl, and cyclohexanoyl).

The term "amino" represents $C_{1-6}$ alkyl, $C_{6-10}$ aryl, $C_{2-6}$ alkenyl, $C_{2-6}$ alkynyl, or $C_{7-12}$ aralkyl groups, unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro, wherein the carbon atoms are covalently bonded to an adjacent element through a nitrogen atom (e.g., pyrrolidine). They include primary, secondary and tertiary amines and quaternary ammonium salts.

The term "aryl" represents an aromatic moiety which may be substituted by hydroxy, $N_3$, CN, halogen (F, Cl, Br, I) and containing at least one benzenoid-type ring, the group may contain from 6 to 14 carbon atoms (e.g., phenyl and naphthyl), particularly 6 to 10 carbon atoms.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. Suitable protecting groups are described, for example, in Greene, et al., "Protective Groups in Organic Synthesis," John Wiley and Sons, Second Edition, 1991, hereby incorporated by reference.

The present invention includes the formation of crystalline cis 2'-deoxy-3'-oxa-4'-thiocytidine, enriched in the desired enantiomer, without requiring the use of seed crystals of desired enantiomer.

The present invention also includes the formation of crystalline cis 2'-deoxy-3'-oxa-4'-thiocytidine using a seed crystal of the desired enantiomer.

The present invention also includes the formation of crystalline cis 2'-deoxy-3'-oxa-4'-thiocytidine starting from cis/trans mixtures of 2'-deoxy-3'-oxa-4'-thiocytidine, wherein the cis to trans ratio is between about 1/1 to about 5/1.

The present invention includes an entrainment process. Firstly, a saturated solution of the racemic cis 2'-deoxy-3'-oxa-4'-thiocytidine or a derivative is prepared at a given temperature. Of particular interest are solvents which favor the crystallization of the product of formula (B). Suitable solvents include water, methanol, ethanol, toluene, tert-butyl methyl ether, isopropanol, n-propanol, acetone or combinations thereof. In an embodiment of the present invention an amount of racemic mixture of cis 2'-deoxy-3'-oxa-4'-thiocytidine or a derivative thereof is dissolved or suspended in a suitable solvent. Heat may be used to complete the dissolution. Concentrations above the saturation point may be used. The conglomerate is formed by adding in excess an achiral acid such as para-toluenesulfonic acid or malic acid or mixtures thereof to the solution or suspension of the 2'-deoxy-3'-oxa-4'-thiocytidine or a derivative thereof to form a salt. The amount of achiral acid used is greater than about 1 eq. The amount of achiral acid may be between about 1 and about 3 eq. The conglomerate salt may be crystallized by conventional means. The melting point of the conglomerate salt is about 20° C. lower than the melting point of the single enantiomer salt. The eutectic point of the para-toluenesulfonic acid salt of 2'-deoxy-3'-oxa-4'-thiocytidine is between about 185° C. and 187° C. The eutectic point of the malic salt of 2'-deoxy-3'-oxa-4'-thiocytidine is between about 171° C. and 173° C.

Once the conglomerate salt is formed the reaction mixture may be seeded with crystals of the desired single enantiomer salt or the mixture may proceed to crystallization by conventional means. The seeded or unseeded mixture is then cooled and once crystallization has taken place, the precipitate product is harvested. The precipitate product shows a greater weight excess of desired single enantiomer salt. The mother liquor shows an excess of the enantiomer (opposite to that used for the seeding if seeding was used).

The precipitate product may be recrystallized by resuspending the precipitate product in a suitable recrystallization solvent. Suitable recrystallization solvents may include alcohols such as methanol, ethanol, isopropanol, acetone, and combinations thereof.

To obtain the free base, the precipitate product is resuspended in a suitable recrystallization solvent. Suitable recrystallization solvents may include alcohols such as methanol, ethanol, isopropanol, acetone, and combinations thereof. If necessary, the pH is adjusted so that the mixture is basic (pH≧7). A base is used to remove the acid. The base may be a free amine such as triethylamine, diethylcyclohexylamine, diethylmethylamine, dimethylethylamine, dimethylisopropylamine, dimethylbutylamine, dimethylcyclohexylamine, tributylamine, diethylmethylamine, dimethylisopropylamine, diisopropylethylamine or combinations thereof, or an immobilized base such as anion exchange resin or even ammonia. If a resin is used, the resin may be removed by filtration. The free base is cooled and the resulting precipitate is dried. The resulting crystalline cis 2'-deoxy-3'-oxa-4'-thiocytidine is enriched in the desired enantiomer. The amount of base added should be sufficient to remove all of the acid counter ion.

The mother liquors resulting from the above described procedure contain an excess of one enantiomer that can be re-subjected to the above procedure but seeding with the opposite enantiomer. By an iterative process of crystallization (cyclic entrainment), seeding with opposite enantiomers alternately, it is, in principle, possible to separate an amount of racemic 2'-deoxy-3'-oxa-4'-thiocytidine entirely into its enantiomeric components.

In the enantiomeric enrichment (ee) procedure of this invention, the recrystallization may be preformed in a variety of solvents. These solvents can be chosen and the crystallization process induced by conventional techniques that lead to the formation of a supersaturated solution. Examples of such conventional techniques include cooling of a saturated solution, solvent evaporation from a saturated solution, or by employing a counter solvent in which the desired end product, such as cis-2'-deoxy-3'-oxa-4'-thiocytidine, is less soluble.

The present invention additionally includes the preparation of conglomerate salts described above using cis/trans mixtures of 2-substituted 4-substituted 1,3-oxathiolanes, wherein the cis to trans ratio (C/T) is between about 4/1 to about 1/4.

In general, if an enantiomerically enriched mixture or a cis/trans combination (wherein C/T >1) of Compound (B) is to be separated, the process may proceed through the following steps: 1) formation of the conglomerate salt; 2) isolation of the enantiomerically enriched precipitate salt; 3) liberation of the enantiomerically enriched free base (Compound (B)) from the precipitate salt by the reaction of the salt with a proper base; 4) isolation of the enantiomerically enriched Compound (B) precipitate.

An embodiment of the present invention is a process for producing (−)-cis-2-hydroxymethyl-4-(cytosin-1'-yl)-1,3-oxathiolane, comprising:

a) preparing a solution of cis-2-hydroxymethyl-4-(cytosin-1'-yl)-1,3-oxathiolane.achiral acid salt having an enantiomeric excess different than zero;

b) crystallizing substantially (−)-cis-2-hydroxymethyl-4-(cytosin-1'-yl)-1,3-oxathiolane.achiral acid salt;

c) recovering said (−)-cis-2-hydroxymethyl-4-(cytosin-1'-yl)-1,3-oxathiolane.achiral acid salt;

d) converting said (−)-cis-2-hydroxymethyl-4-(cytosin-1'-yl)-1,3-oxathiolane.achiral acid salt into said (−)-cis-2-hydroxymethyl-4-(cytosin-1'-yl)-1,3-oxathiolane or pharmaceutically acceptable salts thereof.

Another embodiment of the present invention is the para-toluenesulfonic acid salt of 2'-deoxy-3'-oxa-4'-thiocytidine having an eutectic point is between about 185° C. and 187° C.

Another embodiment of the present invention is the of the malic salt of 2'-deoxy-3'-oxa-4'-thiocytidine having an eutectic point between about 171° C. and 173° C.

BRIEF DESCRIPTION OF THE DRAWINGS

Various features and attendant advantages of the present invention will be more fully appreciated as the same becomes better understood when considered in conjunction with the accompanying drawings, wherein.

The entire disclosure of all applications, patents and publications, cited above and below, is hereby incorporated by reference.

EXAMPLE 1

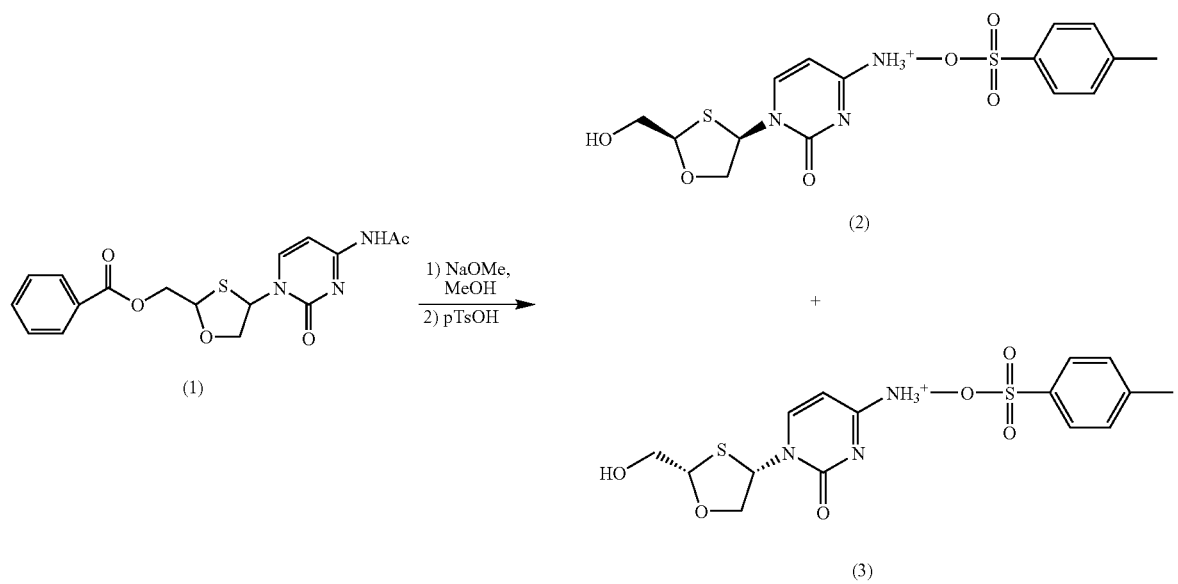

Compound (1) was prepared as described in PCT publication WO 02/102796. Sodium methoxide (0.1 eq) was added in one portion to a methanol suspension (70 mL) of Compound 1 (1.0 eq) at room temperature. The reaction mixture was stirred for 2 hrs at room temperature. TLC analysis (Hexane/EtOAc:1/9) showed the disappearance of starting material and the appearance of the more polar deprotected (1). para-Toluenesulfonic acid (1.14 eq) was added to the solution in one portion at room temperature. The reaction mixture was allowed to stir at room temperature overnight. The reaction mixture was cooled to 0° C.-5° C. The suspension was stirred at this temperature for 1 hour then filtered. The solids were dried to give pure Compounds (2) and (3) as a white solid.

Figure 1:
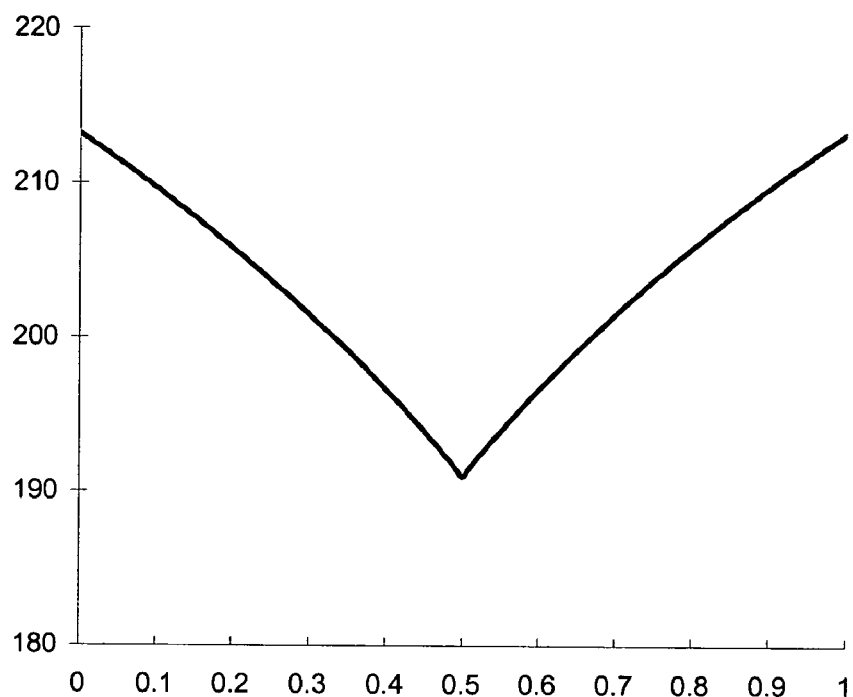
FIG. 1 is a phase diagram of the p-Toluenesulfonic acid salt of Compound (1)

The p-TSA salts of both enantiomers and racemates were prepared and recrystallized from methanol/water/IPA. The maleic acid salt was obtained using the same solvent system. The IR spectra and Differential Scanning Calorimetry (DSC) results are shown in Table 1, Table 2 and FIG. 1.

TABLE 1

| p-TSA Salt | IR Match | DSC data (5° C./min) | |
| | | Melting Point (° C.) | ΔH (J/g) |
| --- | --- | --- | --- |
| Racemate | Yes | 186.8 | 100.2 |
| (−) enantiomer | Yes | 213.2 | 145.6 |
| (+) enantiomer | Yes | 214.2 | |

TABLE 2

| The Maleic Salt | IR Match | DSC data (7° C./min) | |
| | | Melting Point (° C.) | ΔH (J/g) |
| --- | --- | --- | --- |
| Racemate | Yes | 172.0 | — |
| Single enantiomer | Yes | 238.8 | — |

EXAMPLE 2

Figure 2:
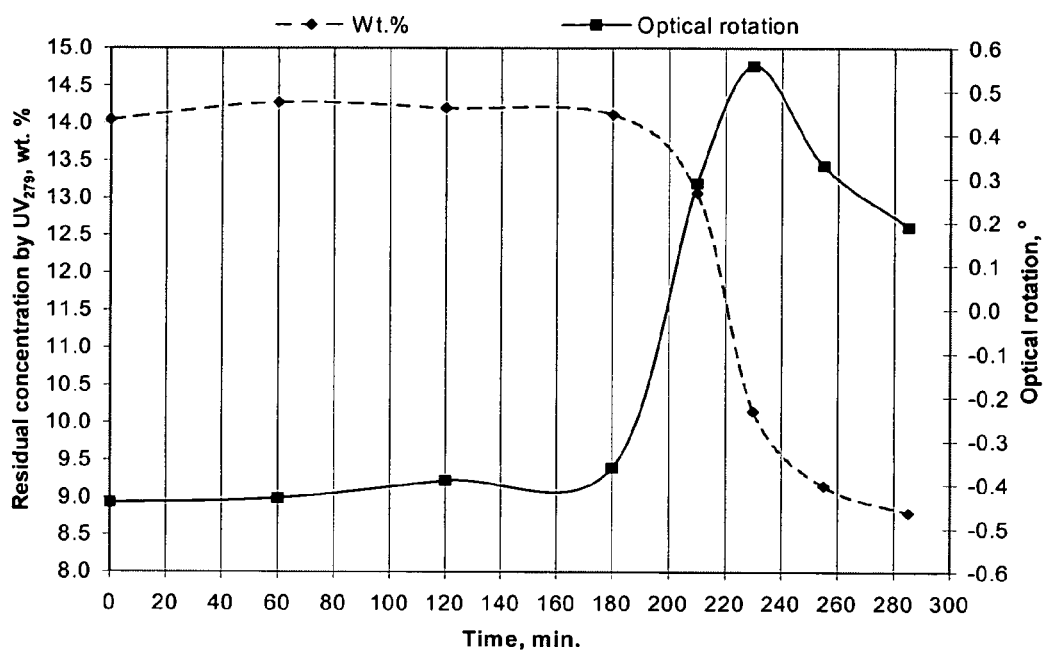
FIG. 2 illustrates the UV and optical rotation monitoring of the crystallization process shown in Example 2.

A 13 wt % racemate mixture of Compound (2) and (3) solution was prepared by dissolving 104.60 g of the racemate in 700 ml water. A 4% e.e. was generated by adding 4.36 g Compound (2) to the mixture. The solids were dissolved by heating the slurry at 50° C. The warm solution was cooled rapidly to 20° C. and then, agitated at this temperature for 1 more hour to ensure its stability. Next, the supersaturated solution was seeded with 202 mg of finely ground Compound (2) (25 mg/100 g solution). The temperature was maintained constant at 20±1° C. with constant agitation. The course of crystallization was monitored by UV at 278 nm and polarimetry (see FIG. 2 below).

The optical rotation of the starting supersaturated solution was −0.44°. A 3-hour induction period was recorded before the crystallization occurred. Approximately 20 minutes into crystallization, the rotation of the solution dropped to zero. Further, the rotation changed sign and reached the maximum of +0.56° after about 50 minutes of crystallization. Changing rotation sign of the supernatant solution indicates that entrainment and resolution has occurred. The solids were filtered out and the optical purity determined. The isolated solid had a higher optical purity than the initial supersaturated solution.

EXAMPLE 3

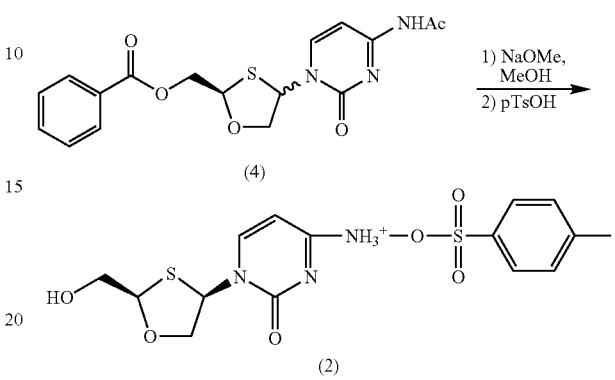

Sodium methoxide (0.1 eq) was added in one portion to a methanol suspension of Compound (4) (1.0 eq, C/T=3.04/1, 95% ee, 96.6% purity) at room temperature. The reaction mixture was stirred for 2 hrs at room temperature. TLC analysis (Hexane/EtOAc:1/9) showed the disappearance of starting material (Rf 0.10 (trans) and 0.16 (cis)) and the appearance of the more polar deprotected Compound (4) (Rf 0.00). The para-toluenesulfonic acid (1.14 eq) was added to the solution in one portion at room temperature. The reaction mixture was allowed to stir at room temperature overnight then filtered. The solids were dried in vacuo to give Compound (2) salt as a white solid (62/1 cis/trans: 98% ee, 85% cis yield corrected).

EXAMPLE 4

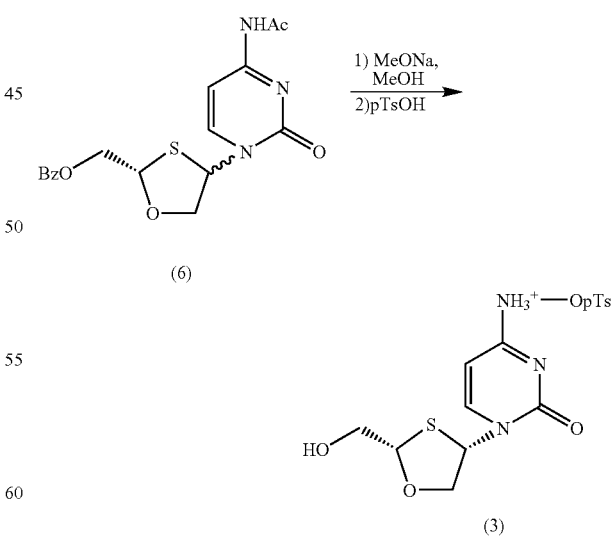

Sodium methoxide (0.1 eq) was added in one portion to a methanol suspension of Compound (6) (1.0 eq, C/T=2.7/1, 95% ee, 96.0% purity) at room temperature. The reaction mixture was stirred for 2 hrs at room temperature. TLC analysis (Hexane/EtOAc:1/9) showed the disappearance of starting material (Rf 0.10 (trans) and 0.16 (cis)) and the appearance of the more polar deprotected Compound (4) (Rf 0.00). para-Toluenesulfonic acid (1.13 eq) was added to the solution in one portion at room temperature. The reaction mixture was allowed to stir at room temperature overnight then filtered. The precipitate was dried in vacuo to give Compound (3) salt as a white solid (62/1 cis/trans: 99% ee, 86% cis yield corrected).

EXAMPLE 5

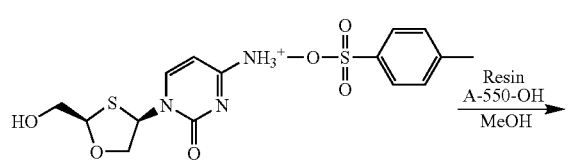

Compound (2) (9.76 mmoles, 1.0 eq) was suspended in methanol at 40° C. Resin DOWEX 550A-OH (140% w/w) was added to the suspension in one portion at 40° C. The reaction mixture was allowed to stir at 40° C. for 2 hrs. The pH of the solution was checked to make sure that it's basic (pH≧7) and a sample was analyzed by $^1$H NMR and showed the disappearance of para-toluenesulfonic acid. The reaction mixture was filtered. The resin was washed with methanol at 40° C. MeOH was distillated and the volume adjusted to 3 volumes. The solution was cooled and precipitation occurred. The suspension was stirred until no additional precipitation was observed then filtered. The solids were dried to give Compound (5) as a white solid (99.7% ee, 82% cis yield).

EXAMPLE 6

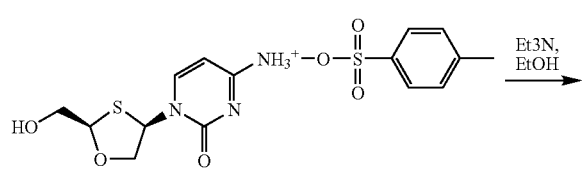

Compound (2) (99.1% ee, C/T=27/1), 6.23 mmoles of cis, 1.0 eq) was suspended in ethanol at 25° C. Triethylamine (9.33 mmoles, 1.5 eq) was added to the suspension in one portion at 25° C. The reaction mixture was heated at 40° C. and stirred for 1 hr at this temperature. The pH of the solution was checked to make sure that it's basic (pH≧7). The solution was cooled and precipitation occurred. The suspension was stirred until no additional precipitation was observed then filtered. The solids were washed with cold ethanol. The solids were dried to give Compound (5) as a white solid (99.4% ee, 80% cis yield).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for the preparation of single enantiomers of a compound of formula (B), and pharmaceutically acceptable salts thereof, in the cis configuration,

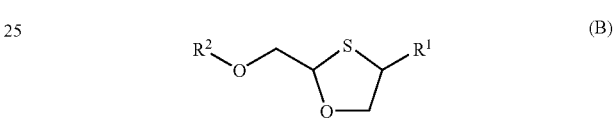

wherein $R^1$ is selected from the following formulae:

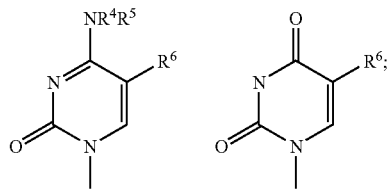

$R^2$ is hydrogen or $R^3$—(CO);

$R^3$ is hydrogen, straight or branched chain alkyl, alkoxyalkyl, aralkyl, aryloxyalkyl, aryl, substituted dihydro pyridinyl, sulphonate esters, sulfate esters, amino acid esters and mono, di- or triphosphate esters;

$R^4$ and $R^5$ are in each case independently H, straight, branched or cyclic $C_{1-6}$ alkyl, straight, branched or cyclic $C_{2-6}$ alkenyl, $C_{6-14}$ aryl, or 5-10 membered heteroaromatic ring containing 1-3 heteroatoms selected from O, N, and S; and $R^6$ is hydrogen, hydroxymethyl, trifluoromethyl, straight, branched or cyclic $C_{1-6}$ alkyl, straight, branched or cyclic $C_{2-6}$ alkenyl, bromine, chlorine, fluorine, or iodine;

said process comprising:

forming a conglomerate salt of a racemic mixture or an enantiomerically enriched mixture of Compound (B) with an acid wherein the resulting conglomerate salt has the following characteristics:

the IR spectrum of the salt of the racemic compound, a 1:1 mixture of (−) and (+) crystals, is identical to each of the single enantiomers, and the salt of the racemic compound has a melting point lower than that of either single enantiomer; and resolving said mixture by preferential crystallization.

2. A process according to claim 1, wherein $R^3$ is methyl, ethyl, n-propyl, t-butyl, n-butyl, methoxymethyl, benzyl, phenoxymethyl, phenyl, phenyl substituted by halogen, $C_{1-4}$ alkyl or $C_{1-4}$ alkoxy.

3. A process according to claim 1, wherein the single enantiomers of the conglomerate salt show a much lower solubility than the racemate of the conglomerate salt in polar solvents.

4. A process according to claim 1, wherein the conglomerate salt of cis 2'-deoxy-3'-oxa-4'-thiocytidine is formed.

5. A process according to claim 1, wherein enantiomer separation of the enantiomeric mixture is performed by seeding a supersaturated solution of the conglomerate salt with the desired single enantiomer.

6. A process according to claim 1, wherein $R^1$ is cytosine or 5-fluorocytosine.

7. A process according to claim 1, wherein said acid is para-toluenesulfonic acid, maleic acid or a mixture thereof.

8. A process according to claim 1, wherein the conglomerate salt of cis 2'-deoxy-3'-oxa-4'-thiocytidine is formed.

9. A process according to claim 2, wherein $R^1$ is cytosine or 5-fluorocytosine.

10. A process according to claim 9, wherein said acid is para-toluenesulfonic acid, maleic acid or a mixture thereof.

11. A process according to claim 1, wherein a conglomerate salt of cis 2'-deoxy-3'-oxa-4'-thiocytidine is formed in which the single enantiomers show a lower solubility than the racemate in polar solvents.

12. A process according to claim 11, wherein said conglomerate salt of cis 2'-deoxy-3'-oxa-4'-thiocytidine is the para-toluenesulfonic acid salt of 2'-deoxy-3'-oxa-4'-thiocytidine having an eutectic point between about 185° C. and 187° C.

13. A process according to claim 11, wherein said conglomerate salt of cis 2'-deoxy-3'-oxa-4'-thiocytidine has an eutectic point between about 171° C. and 173° C.

14. A process according to claim 1, wherein said acid is hydrochloric acid (HCl), hydrobromic acid (HBr), sulfuric acid ($H_2SO_4$), tetrafluoroboric acid ($HBF_4$), methanesulfonic acid ($CH_3SO_3H$), benzenesulfonic(BS) acid ($C_6H_5SO_3H$), p-toluenesulfonic acid (p-$CH_3C_6H_4SO_3H$), p-aminoBS acid (p-$NH_2C_6H_4SO_3H$), p-chloroBS acid (p-$ClC_6H_4SO_3H$), p-hydroxyBS acid (p-$HOC_6H_4SO_3H$), chloroacetic acid ($ClCH_2COOH$), dichloroacetic acid ($Cl_2CHCOOH$), trichloroacetic acid ($Cl_3CHCOOH$), glycolic acid ($HOCH_2COOH$), pyruvic acid ($CH_3COCOOH$), succinic acid ($HOOC(CH_2)_2COOH$), adipic acid, ($HOOC(CH_2)_4COOH$), maleic acid (Cis-HOOCCH=CHCOOH), fumaric acid (Tr-HOOCCH=CHCOOH), or citric acid ($HOC(CO_2H)(CH_2CO_2H)_2$).

15. A process according to claim 1, wherein
said racemic mixture or enantiomerically enriched mixture of Compound B is a mixture of cis-2-hydroxymethyl-4-(cytosin-1'-yl)-1,3-oxathiolane or a salt thereof;
said forming of a conglomerate salt comprises:
a) reacting said mixture of cis-2-hydroxymethyl-4-(cytosin-1'-yl)-1,3-oxathiolane with an achiral acid to produce cis-2-hydroxymethyl-4-(cytosin-1'-yl)-1,3-oxathiolane.achiral acid salt; and
said resolving of said mixture comprises:
b) preparing a solution of cis-2-hydroxymethyl-4-(cytosin-1'-yl)-1,3-oxathiolane.achiral acid salt having an enantiomeric excess greater than zero;
c) adding to said solution an amount of (+) or (−)-cis-2-hydroxymethyl-4-(cytosin-1'-yl)-1,3-oxathiolane.achiral acid salt sufficient to initiate crystallization;
d) recovering substantially one of said (+) or (−)-cis-2-hydroxymethyl-4-(cytosin-1'-yl)-1,3-oxathiolane.achiral acid salt; and
e) converting said (+) or (−)-cis-2-hydroxymethyl-4-(cytosin-1'-yl)-1,3-oxathiolane.achiral acid salt into (+) or (−)-cis-2-hydroxymethyl-4-(cytosin-1'-yl)-1,3-oxathiolane or salts.

16. A process according to claim 1, wherein $R^3$ is selected from hydrogen, straight or branched chain alkyl, alkoxyalkyl, aralkyl, aryloxyalkyl, aryl, substituted dihydropyridinyl, alkylsulphonyl, aralkylsulphonyl, sulfate esters, amino acid esters, and mono, di- or triphosphate esters.

17. A process according to claim 1, wherein $R^3$ is hydrogen, methyl, ethyl, n-propyl, t-butyl, n-butyl, methoxymethyl, benzyl, phenoxymethyl, phenyl, phenyl substituted by halogen, $C_{1-4}$ alkyl or $C_{1-4}$ alkoxy, N-methyldihydropyridinyl, methanesulphonyl, L-valyl or L-isoleucyl.

18. A process for the preparation of single enantiomers of a compound of formula (B), and pharmaceutically acceptable salts thereof, in the cis configuration,

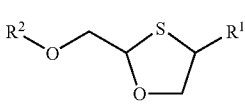

(B)

wherein
$R^1$ is selected from the following formulae:

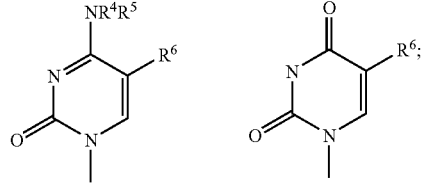

$R^2$ is an ester derived from a dicarboxylic acid of the formula $HO_2C(CH_2)_nCO_2H$ where n is an integer of 1 to 10;
$R^4$ and $R^5$ are in each case independently H, straight, branched or cyclic $C_{1-6}$ alkyl, straight, branched or cyclic $C_{2-6}$ alkenyl, $C_{6-14}$ aryl, or 5-10 membered heteroaromatic ring containing 1-3 heteroatoms selected from O, N, and S; and
$R^6$ is hydrogen, hydroxymethyl, trifluoromethyl, straight, branched or cyclic $C_{1-6}$ alkyl, straight, branched or cyclic $C_{2-6}$ alkenyl, bromine, chlorine, fluorine, or iodine;
said process comprising:
forming a conglomerate salt of a racemic mixture or an enantiomerically enriched mixture of Compound (B) with an acid wherein the resulting conglomerate salt has the following characteristics:
the IR spectrum of the salt of the racemic compound, a 1:1 mixture of (−) and (+) crystals, is identical to each of the single enantiomers, and
the salt of the racemic compound has a melting point lower than that of either single enantiomer; and
resolving said mixture by preferential crystallization.

19. A process according to claim 15, wherein said achiral acid is hydrochloric acid (HCl), hydrobromic acid (HBr), sulfuric acid ($H_2SO_4$), tetrafluoroboric acid ($HBF_4$), methanesulfonic acid ($CH_3SO_3H$), benzenesulfonic(BS) acid ($C_6H_5SO_3H$), p-toluenesulfonic acid (p-$CH_3C_6H_4SO_3H$), p-aminoBS acid (p-$NH_2C_6H_4SO_3H$), p-chloroBS acid (p-$ClC_6H_4SO_3H$), p-hydroxyBS acid (p-$HOC_6H_4SO_3H$), chloroacetic acid ($ClCH_2COOH$), dichloroacetic acid ($Cl_2CHCOOH$), trichloroacetic acid ($Cl_3CHCOOH$), glycolic acid ($HOCH_2COOH$), pyruvic acid ($CH_3COCOOH$), succinic acid ($HOOC(CH_2)_2COOH$), adipic acid, ($HOOC(CH_2)_4COOH$), maleic acid (Cis-HOOCCH=CHCOOH), fumaric acid (Tr-HOOCCH=CHCOOH), or citric acid ($HOC(CO_2H)(CH_2CO_2H)_2$).

20. A process according to claim 6, wherein $R^1$ is cytosine.

21. A process according to claim 6, wherein $R^1$ is 5-fluorocytosine.

22. A process according to claim 10, wherein $R^1$ is cytosine.

23. A process according to claim 10, wherein $R^1$ is 5-fluorocytosine.

* * * * *

UNITED STATES PATENT AND TRADEMARK OFFICE
CERTIFICATE OF CORRECTION

PATENT NO. : 7,501,514 B1  Page 1 of 1
APPLICATION NO. : 10/964975
DATED : March 10, 2009
INVENTOR(S) : Dragos Vizitiu It is certified that error appears in the above-identified patent and that said Letters Patent is hereby corrected as shown below:

Column 12, line 47, reads "esters and mono," should read -- esters and mono- --
Column 13, lines 59-60, reads "-oxathiolane.achiral" should read
-- -oxathiolane·achiral --
Column 13, line 63, reads "-oxathiolane.achiral" should read -- -oxathiolane·achiral --
Column 13, lines 66-67, reads "-oxathiolane.achiral" should read
-- -oxathiolane·achiral --
Column 14, lines 2-3, reads "-oxathiolane.achiral" should read
-- -oxathiolane·achiral --
Column 14, line 5, reads "-oxathiolane.achiral" should read -- -oxathiolane·achiral --
Column 14, line 12, reads "mono, di- or" should read -- mono- di- or --

Signed and Sealed this

Twenty-seventh Day of October, 2009

David J. Kappos
*Director of the United States Patent and Trademark Office*